United States Patent [19]
Nielsen et al.

[11] Patent Number: 5,882,715
[45] Date of Patent: Mar. 16, 1999

[54] METHOD OF PREPARING AN ORAL PREPARATION PROVIDED ON THE OUTER SIDE WITH AN ENTERIC COATING, AS WELL AS AN ORAL PREPARATION OBTAINED BY THE METHOD

[75] Inventors: Nils Villadsen Nielsen, Aylum; Elsebeth Marcher Holm, Hundested; Hans Holmen, Brøndby; Arne Martinus Pedersen, Vanløse, all of Denmark

[73] Assignee: Pharma-Vinci A/S, Ffrederiksvaerk, Denmark

[21] Appl. No.: 981,622

[22] PCT Filed: Jun. 19, 1996

[86] PCT No.: PCT/DK96/00267

§ 371 Date: Dec. 15, 1997

§ 102(e) Date: Dec. 15, 1997

[87] PCT Pub. No.: WO97/00674

PCT Pub. Date: Jan. 9, 1997

[30] Foreign Application Priority Data

Jun. 20, 1995 [DK] Denmark ................. 0698/95

[51] Int. Cl.$^6$ ................. A61J 3/00; A61K 9/36; A61K 9/38; A61K 9/42
[52] U.S. Cl. .......... 427/2.16; 427/2.19; 427/2.21; 427/426; 424/457; 424/460; 424/461; 424/463; 424/472; 424/476; 424/477; 424/479; 424/491; 424/493
[58] Field of Search ................. 427/2.15, 2.19, 427/2.21, 426, 2.16, 2.22, 424; 424/463, 490, 491, 493, 471, 477, 479, 439, 457, 460, 461, 468, 476, 472

[56] References Cited

U.S. PATENT DOCUMENTS

| | | |
|---|---|---|
| 3,922,339 | 11/1975 | Shear ................. 427/2.21 |
| 4,309,404 | 1/1982 | DeNeale et al. ............ 424/21 |
| 4,384,004 | 5/1983 | Cea et al. ................. 426/3 |
| 4,687,676 | 8/1987 | Wu et al. ................. 427/2.21 |
| 4,716,041 | 12/1987 | Kjornes et al. ........... 427/2.21 |
| 4,828,840 | 5/1989 | Sakamoto et al. ........ 427/2.21 |
| 5,225,238 | 7/1993 | Ardaillon et al. ........ 427/2.21 |
| 5,445,829 | 8/1995 | Paradissis et al. ....... 427/2.21 |
| 5,505,983 | 4/1996 | Kamada ................. 427/2.21 |
| 5,679,377 | 10/1997 | Bernstein et al. ........ 427/2.21 |
| 5,700,484 | 12/1997 | Chauffard et al. ....... 427/2.19 |

FOREIGN PATENT DOCUMENTS

| | | |
|---|---|---|
| 0454287 | 10/1991 | European Pat. Off. . |
| 995437 | 6/1965 | United Kingdom ........ 424/477 |

OTHER PUBLICATIONS

C.B. Abletshauser, et al., "Film Coating of Pellets with Insoluble Polymers Obtained in Situ Crosslinking in the . . . " Journal of Controlled Release, vol. 27, 1993, pp. 149–156 (no month).

A. Polk, et al., "Controlled Release of Albumin from Chitosan–Alginate Microcapsules" Journal of Pharmaceutical Sciences, vol. 83, No. 2, Feb. 1994, pp. 178–185.

*Primary Examiner*—Diana Dudash
*Attorney, Agent, or Firm*—Ladas & Parry

[57] ABSTRACT

A method of preparing an oral preparation, especially in the form of hard gelatin capsules, tablets or pellets, for use by the administration of drugs or supplementary nutrients for human beings or animals, said preparation on its outer side being provided with an enteric coating which contains or comprises a calcium salt of a polysaccharide. A moisture-resistant layer containing a protein, especially zein, can be provided between the material to be coated and the enteric coating. The enteric coating is formed in situ by spraying the liquid coating substances in a fluidized bed. The present invention also pertains to oral preparations which is prepared by the method.

7 Claims, No Drawings

METHOD OF PREPARING AN ORAL PREPARATION PROVIDED ON THE OUTER SIDE WITH AN ENTERIC COATING, AS WELL AS AN ORAL PREPARATION OBTAINED BY THE METHOD

TECHNICAL FIELD

The present invention relates to a method of preparing an oral preparation, especially in the form of hard gelatin capsules, tablets, powders or pellets, said preparation on the outer side being provided with an enteric coating resistant to the acid environment in the stomach and containing or comprising a calcium salt of a polysaccharide, where a moisture-resistant layer containing a protein is provided between the material to be coated and the coating applied and optionally also on the outer side of the coating. The method according to the invention is characterised in that the enteric coating is formed in a fluidized bed, where both a liquid containing calcium ions and a liquid containing the anion of a soluble salt of a polysaccharide are sprayed onto the material to be coated.

BRIEF DESCRIPTION OF THE INVENTION

The oral preparation prepared according to the invention is a solid substance, for instance in form of tablets, capsules, pellets, powders or granules to be used by the administration of drugs or supplementary nutrients for human beings or animals, a coating in form of an enteric film being applied onto said solid substance. To be more precise, a coating is applied onto the solid substance, said coating being of such a nature that upon administration to a human being or an animal said coated substance is substantially unaffected by chemical, enzymatic or other conditions prevailing in the stomach while said substance passes through this portion of the digestive system. Subsequently, the substance is, however, in the process of dissolution or is disintegrating in another manner in the intestinal canal with the result that the drug or supplementary nutrients contained in the solid substance are released. Such preparations are also known as for instance "gastro-resistant", "entero-soluble", "enterically coated", or simply "enteric" preparations.

Many situations apply where it is very important or at least advisable to provide an enteric film coating on preparations to be orally administered.

Such situations are for instance the following:

(1) It can be essential to ensure that a substance, such as a solid substance, contained in the preparation remains intact until it reaches the absorption site in the intestinal canal without having been subjected to a previous disintegration in the stomach. Thus, several drugs of major medicinal importance, such as some antibiotics and some antiinflammatory and antineoplastic agents are easily and quickly decomposed under the chemical and enzymatic conditions or other conditions prevailing in the gastric juices of human beings and animals, whereby these drugs lose their therapeutical effect before they reach the absorption site. Therefore it is necessary to ensure that such drugs for oral administration are able to resist the passage through the stomach in such a manner that they can remain intact until they reach the intestinal canal and without losing the desired effect. Preparations are also known which contain live (such as freeze-dried) bacteria, such as Lactobacillus acidophilus, which cannot survive the low pH-values in the stomach. Such live bacteria are used for the prevention or treatment of stomach infections.

(2) It can be necessary to protect persons using drugs against dyspeptic adverse effects, such as ulcerogenic effects related to the taking in of drugs such as acetylsalicylic acid (which is widely used as an analgetic and also increasingly used for the prevention or therapeutical treatment of cardiovascular diseases), sodium chloride (which for instance is used instead of physiological salt), potassium chloride (which is orally administered in connection with treatment with diuretics or as a replacement of sodium chloride) or ammonium chloride (which for instance is used for the treatment of metabolic baseosis).

(3) A demand is found in obtaining a high local concentration of for instance an antiinflammatory agent or a digestive enzyme in a specific location in the intestinal system in order to provoke a specific, local effect.

(4) Furthermore, it can be important to encapsulate a substance having an unpleasant taste or smell or which at release in the stomach can be nauseating or cause other undesired effects in order to ensure that said substance is not released until it has passed the stomach whether or not the substance in question is disintegrated by the gastric juices.

The agents previously used for this purpose include polyvinyl acetate-phthalate, methacrylacid ester derivatives, such as "Eudragit", and hydroxypropylmethyl cellulose derivatives. Some of these agents have been accepted for use as enteric films for the coating of drugs, but the physiological effect resulting from administration for a long time of such agents is generally unknown, and only a few of these agents have been accepted for an enteric coating of foodstuffs or over-the-counter drugs and supplementary nutrients.

Thus a demand exists for providing a safe and reliable enteric coating to be used in connection with drugs and supplementary nutrients for oral administration, said coating being prepared from ingredients having well-researched physiological properties and a good compatibility. This demand is met by the present invention, because the method according to the invention has the effect that on the outer side of the oral preparation an enteric coating is provided, said coating being resistant to the acid conditions prevailing in the stomach and containing or comprising a calcium salt of a polysaccharide, especially calcium pectinate or calcium alginate. Freeze-dried lactic acid bacteria are as already mentioned sensitive to the low pH-values of the magnitude prevailing in the stomach of human beings and animals. It is therefore necessary to protect the bacteria against the effect of the lactic acid while the preparation is passing through said stomach. The latter is according to the invention accomplished by coating the preparation, such as capsules, tablets, powders or pellets, with a coating which is insoluble in acid, but soluble under the neutral or slightly alkaline conditions prevailing in the small intestine. Concerning the pH-conditions in the stomach-intestinal system reference is made to D. F. Evans et al., Gut 29, 1035–1041 (1988), J. Fallingborg et al., J. Pediatr. Gastroenterol. Nutr. 11(2), 211–214 (1990) and J. B. Dressman, Pharm. Res. 3 (3), 123–131 (1986).

Many disintegrating processes are accelerated by the presence of moisture, which has for instance been determined by stability tests with tablets and capsules. As far as freeze-dried bacteria are concerned it is a fact that the survival of many species depends highly on dry conditions.

Therefore a moisture-resistant layer containing protein is provided between the material to be administered, such as a drug or a supplementary nutrient, and the enteric coating.

Such a moisture-resistant, water-stopping layer can furthermore be placed on the outer side of the preparation, i.e. on the surface of the enteric coating. A particularly suited protein for this purpose is zein, which is only soluble in 85 vol % aqueous alcohol. The low water content renders this solvent suited because the solvent of the protein must not contain too much water as water might otherwise be transferred to the material to be administered.

The use of polysaccharides capable of undergoing a cross-linking by means of cations is known from a number of publications. Thus JP-A2-04036159 describes a soft capsule, which among other things contain pectin and calcium. Soft capsules present, however, limited applications because they are not suited for use for instance in connection with live bacteria.

JP-A2-04027352 describes also soft capsules containing polysaccharides cross-linked by means of calcium ions. These soft capsules are used for health food products and are produced by a calcium salt and one or more water-soluble polysaccharides being mixed into a film substrate comprising gelatin and a plasticizer, in a rotating apparatus for the production of capsules.

CN Patent Application No. 87-101114 deals with a method of coating tablets, where the coating is performed in a coating pan by means of powdered sodium alginate in combination with a syrup followed by the applied layer being treated with a calcium chloride solution. The coating in a coating pan is, however, a process encumbered with some draw-backs, such as a long processing period, high moisture, and the necessity of using a specially trained staff, and this process is not suited for coating hard gelatin capsules.

A method of coating tablets with calcium alginate is described in Drug Development and Industrial Pharmacy 20(3), 378–394 (1994). The tablets are immersed into an aqueous solution of sodium alginate, said tablets containing calcium acetate disintegrating and forming a cross-linking with the alginate while forming a coating on said tablets. A draw-back is, however, found in the tablets being exposed to water, and in the resulting coating not being smooth. Moreover, the method cannot be used on capsules, but only on tablets.

The method according to the invention overcomes these draw-backs.

A method related to the method according to the present invention is disclosed in Journal of Controlled Release 27 (1993), 149–156. However, the object of the coating according to this citation is to achieve a pH independent release of the drug. The enteric coating according to the invention aims at achieving the opposite effect, i.e. the release of the drug being dependent on the pH value. More specifically, the purpose is at acidic pH values to achieve protection against intrusion of liquid into the preparation or protection against exudation of substance from the preparation, whereas at neutral or weakly basic pH values a quick release of the substance is desired. This objective is not met with the coating disclosed in the above citation.

By the method according to the invention, the enteric coating is as mentioned formed in a fluidized bed where a liquid containing calcium ions and a liquid containing the anion of a soluble salt of a polysaccharide are sprayed onto the material to be coated. The coating is performed in a fluidizing apparatus equipped with two or more nozzles for the spraying of the liquids, the enteric coating being formed in situ by a reaction between the content of one liquid of polysaccharide anions and the content of the other liquid of $Ca^{2+}$ ions.

Thus the apparatus used employs at least two nozzles, but as three different liquids are used an advantage is found in providing the apparatus with three nozzles because a change from the zein solution to an aqueous solution otherwise requires a preceding cleaning of the entire hose system by means of an aqueous alcohol in order to avoid a clogging.

The invention is illustrated in greater detail by means of the following Examples:

EXAMPLE 1

An enteric film coating is formed on capsules and tablets in a fluidizing apparatus with three nozzles (EB Laboratorie-Coater from EB-Teknik, Borup, DK). The coating comprises three layers: One inner layer, an intermediary layer, and an outer layer.

Three suspensions of the following compositions are applied:

|  | % |
|---|---|
| Suspension 1 | |
| Zein | 8.34 |
| Stearic acid | 4.2 |
| Olive oil | 4.2 |
| Ethanol, 96% | 70.0 |
| Purified water | 13.26 |
| Suspension 2 | |
| Sodium alginate | 4 |
| Magnesium stearate | 0.25 |
| Olive oil | 0.375 |
| Purified water | 95.375 |
| Suspension 3 | |
| Calcium gluconate | 10 |
| Purified water | 90 |

For every $cm^2$ tablet or capsule, the following amounts of the above suspensions are applied:

|  | Nozzle 1 | Nozzle 2 | Nozzle 3 |
|---|---|---|---|
| Inner layer | 15 mg susp. 1 | | |
| Intermediary layer | | 80 mg susp. 2 | 22 mg susp. 3 |
| Outer layer | 5 mg susp. 1 | | |

Inner layer: Suspension 1 is sprayed thereon

Intermediary layer: The suspensions 2 and 3 are sprayed through their respective nozzles.

Outer layer: Suspension 1 is sprayed thereon.

EXAMPLE 2

In an apparatus as described in Example 1 a coating is performed of hard gelatin capsules in a fluidized bed by means of 3 nozzles, 1 nozzle being used for each of the following suspensions.

|  | % |
|---|---|
| Zein suspension | |
| Zein | 8.34 |
| Stearic acid | 4.20 |
| Olive oil | 4.20 |
| Ethanol, 96% | 70.00 |

-continued

|  | % |
| --- | --- |
| Purified water | 13.26 |
| Alginate suspension | |
| Sodium alginate | 4.00 |
| Magnesium stearate | 0.25 |
| Olive oil | 0.375 |
| Purified water | 95.375 |
| Ca-gluconate suspension | |
| Calcium gluconate | 10.00 |
| Purified water | 90.00 |

Initially, the capsules are heated to a temperature of 38° to 43° C., whereafter a layer of the zein suspension is applied, which counteracts the penetration of water during the further coating. Input temperature: 50° to 60° C.; output temperature: 39° to 43° C. Nozzle pressure: approximately 4 bar.

In the following step the capsules are provided simultaneously through 2 nozzles with a layer of the alginate suspension and a layer of the calcium gluconate suspension. Input temperature: 65° to 75° C.; output temperature: 39° to 43° C. Nozzle pressure: approximately 4 bar.

Finally the capsules are provided with yet another layer of the zein suspension. Input temperature: 50° to 60° C.; output temperature: 39° to 43° C. Nozzle pressure: approximately 4 bar. As a result, a tight surface is obtained.

After the coating, the capsules are cooled.

EXAMPLE 3

The following test illustrates that the protein zein counteracts penetration of water into the material to be coated.

An enteric film coating is applied to hard gelatin capsules in an apparatus as mentioned in Example 1. The coating comprises four layers: One inner layer, 2 intermediary layers (2 and 3), and an outer layer.

Three suspensions of the following compositions are applied:

|  | % |
| --- | --- |
| Suspension 1 | |
| Zein | 8.34 |
| Stearic acid | 4.20 |
| Olive oil | 4.20 |
| Ethanol, 96% | 70.00 |
| Purified water | 13.26 |
| Suspension 2 | |
| Sodium alginate | 4.00 |
| Magnesium stearate | 0.25 |
| Olive oil | 0.375 |
| Purified water | 95.375 |
| Suspension 3 | |
| Calcium gluconate | 10.00 |
| Purified water | 90.00 |

For every cm² capsule surface the following amounts of the above suspensions are applied:

|  | Nozzle 1 | Nozzle 2 | Nozzle 3 |
| --- | --- | --- | --- |
| Inner layer | 5 mg susp. 1 | | |
| Layer 2 | 10 mg susp. 1 | 8 mg susp. 2 | |
| Layer 3 | | 80 mg susp. 2 | 22 mg susp. 3 |
| Outer layer | 5 mg susp. 1 | | |

Input temperature: 50° to 70° C.; output temperature: 40° to 42° C. Nozzle pressure: approximately 4 bar.

As an expression of the counteracting of water penetration into the capsules, the so-called aw value is used:

|  | aw |
| --- | --- |
| Before coating | 0.14 |
| After coating | 0.26 |

By way of comparison, the following amounts of the above suspensions are instead applied per cm² of capsule surface:

|  | Nozzle 1 | Nozzle 2 | Nozzle 3 |
| --- | --- | --- | --- |
| Inner layer | 15 mg susp. 1 | 12 mg susp. 2 | |
| Intermediary layer | | 80 mg susp. 2 | 22 mg susp. 3 |
| Outer layer | 5 mg susp. 1 | | | in such a manner that the inner layer contains both zein and sodium alginate suspensions. The following result applies:

|  | aw |
| --- | --- |
| Before coating | 0.14 |
| After coating | 0.40 |

Three nozzles are used in the apparatus in order to avoid a cleaning of the hose system when changing from zein solution to an aqueous solution. The use of only two nozzles would furthermore necessitate a thorough cleaning of the hose system when changing from calcium gluconate to sodium alginate due to the risk of formation of insoluble calcium alginate.

We claim:

1. A method of preparing an oral preparation to be used for the administration of drugs or supplementary nutrients for human beings or animals, the outer surface of said preparation being provided with an enteric coating which is resistant to the acid environment in the stomach and which contains or comprises a calcium salt of a polysaccharide, said method comprising the following steps:

(a) applying a moisture-resistant layer on the material to be coated by spraying a liquid containing a protein and stearic acid on the material, (b) providing an enteric coating upon the moisture-resistant layer by spraying in a fluidized bed, where a liquid containing calcium ions and another liquid containing the anion of a soluble salt of a polysaccharide are applied from separate nozzles, and (c) optionally applying a second moisture-resistant layer containing a protein upon the enteric coating by spraying in situ.

2. A method as claimed in claim 1, wherein the coating is performed in a fluidizing apparatus equipped with two or more nozzles for the spraying of the liquids, and that the enteric coating is formed in situ by a reaction between the content of one liquid of polysaccharide-anions and the content of the other liquid of $Ca^{2+}$ ions.

3. A method as claimed in claim 1 wherein the calcium salt is calcium pectinate or calcium alginate.

4. A method as claimed in claim 1, wherein the protein is zein.

5. An oral preparation to be used for the administration of drugs or supplementary nutrients for human beings or animals, said preparation on the outer side being provided with an enteric coating, wherein the oral preparation is prepared by a method as claimed in claim 1.

6. A method according to claim 1, wherein the oral preparation is in the form of a hard gelatin capsule, tablet, powder or pellet.

7. The oral preparation according to claim 5, in the form of a hard gelatin capsule, tablet, powder or pellet.

* * * * *